United States Patent
Gupta et al.

(10) Patent No.: US 7,040,485 B2
(45) Date of Patent: May 9, 2006

(54) METHOD AND APPARATUS FOR PACKAGING A DRUG-DEVICE COMBINATION PRODUCT

(75) Inventors: Rainuka Gupta, Cambridge, MA (US); Alan J. Dextradeur, Franklin, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 0 days.

(21) Appl. No.: 11/174,115

(22) Filed: Jul. 1, 2005

(65) Prior Publication Data

US 2005/0241981 A1    Nov. 3, 2005

Related U.S. Application Data

(62) Division of application No. 10/676,333, filed on Sep. 30, 2003.

(51) Int. Cl.
*B65D 73/00* (2006.01)

(52) U.S. Cl. .............. 206/484.1; 206/524.8; 206/438; 53/425; 53/434; 383/102

(58) Field of Classification Search ............. 206/484, 206/484.1, 524.1, 524.8, 438, 210, 205; 53/425, 53/434, 469, 449; 383/102, 109
See application file for complete search history.

(56) References Cited

U.S. PATENT DOCUMENTS

| | | | |
|---|---|---|---|
| 2,917,878 A | * | 12/1959 | Carnarius et al. ............ 53/426 |
| 2,947,415 A | * | 8/1960 | Garth ......................... 206/364 |
| 3,613,879 A | * | 10/1971 | Kemble ...................... 206/210 |
| 3,726,057 A | | 4/1973 | Kemble |
| 3,815,315 A | * | 6/1974 | Glick .......................... 53/425 |
| 4,603,538 A | | 8/1986 | Shave |
| 4,644,586 A | | 2/1987 | Padgett |
| 4,709,819 A | | 12/1987 | Lattuada et al. |
| 4,714,595 A | * | 12/1987 | Anthony et al. ............ 422/294 |
| 4,756,140 A | | 7/1988 | Gannon |
| 4,813,210 A | | 3/1989 | Masuda et al. |
| 4,941,308 A | | 7/1990 | Grabenkort et al. |
| 4,949,529 A | | 8/1990 | Davis |
| 5,009,318 A | * | 4/1991 | Lepinoy ................... 206/524.8 |
| 5,014,494 A | | 5/1991 | George |
| 5,103,618 A | | 4/1992 | Garwood |
| 5,354,569 A | | 10/1994 | Brown et al. |

(Continued)

FOREIGN PATENT DOCUMENTS

EP    0492399 A3    7/1992

(Continued)

*Primary Examiner*—Jila M. Mohandesi

(57) ABSTRACT

A package for a drug-device combination product includes an outer package including a first gas impermeable sheet and a second gas impermeable sheet hermetically sealed there to on three sides. A gas permeable header is attached to an unsealed side of the first sheet and sealed to the second sheet on two sides. The first and second gas impermeable sheets and the header form an interior and an opening communicating with the interior. A gas permeable inner package is disposed within the outer package. A product is sealed within the inner package. The inner package is placed within the outer package and a top end of the header is sealed to the second sheet. The outer package is then sealed by sealing the first gas impermeable sheet to the second gas impermeable sheet at a seal point below the point where the header attaches to the first sheet.

15 Claims, 8 Drawing Sheets

U.S. PATENT DOCUMENTS

| | | |
|---|---|---|
| 5,551,557 A * | 9/1996 | Brooks et al. ............... 206/205 |
| 5,577,368 A | 11/1996 | Hamilton et al. |
| 5,578,075 A | 11/1996 | Dayton |
| 5,624,704 A | 4/1997 | Darouiche |
| 5,879,620 A | 3/1999 | Cohen |
| 6,161,695 A | 12/2000 | Nicolais |
| 6,174,934 B1 | 1/2001 | Sun et al. |
| 6,705,061 B1 * | 3/2004 | Porret et al. .................. 53/425 |
| 2002/0062147 A1 | 5/2002 | Yang |

FOREIGN PATENT DOCUMENTS

| | | |
|---|---|---|
| WO | WO 03/009777 A3 | 2/2003 |

* cited by examiner

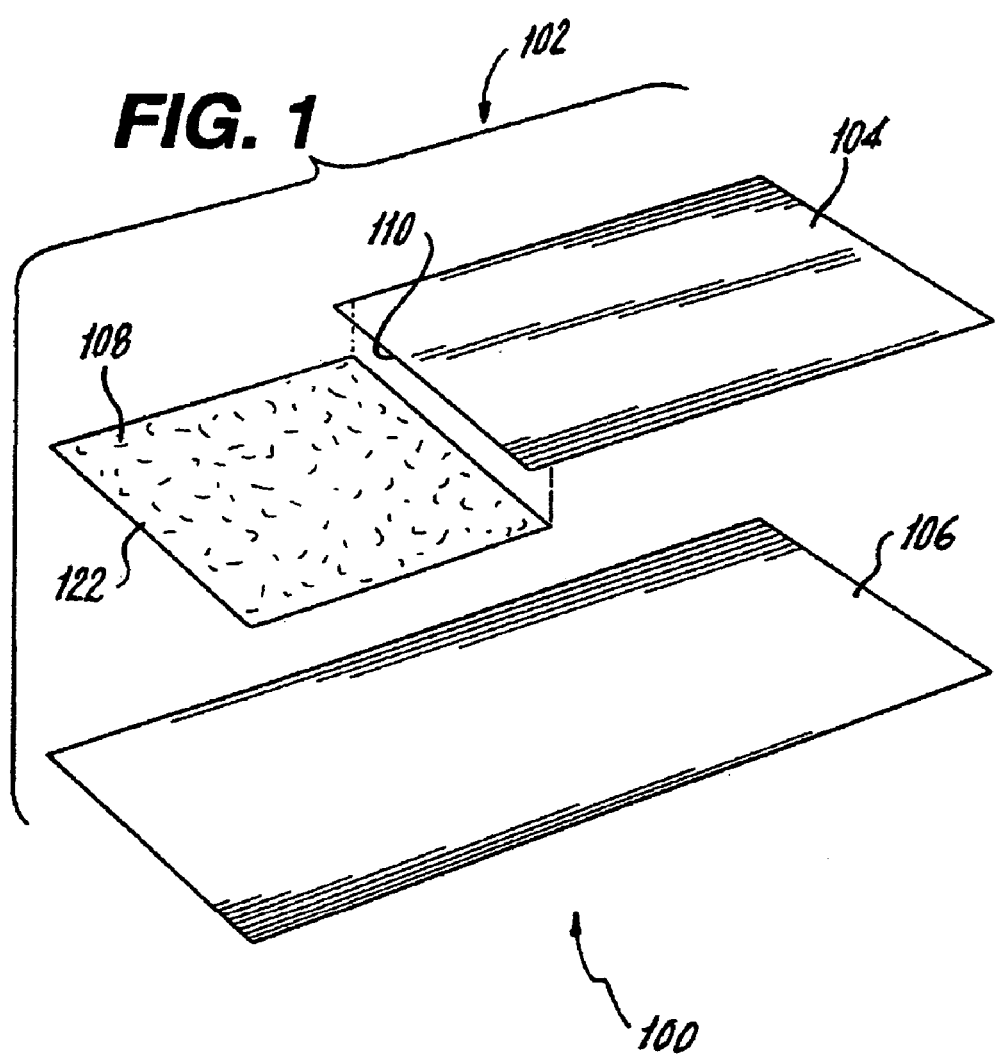

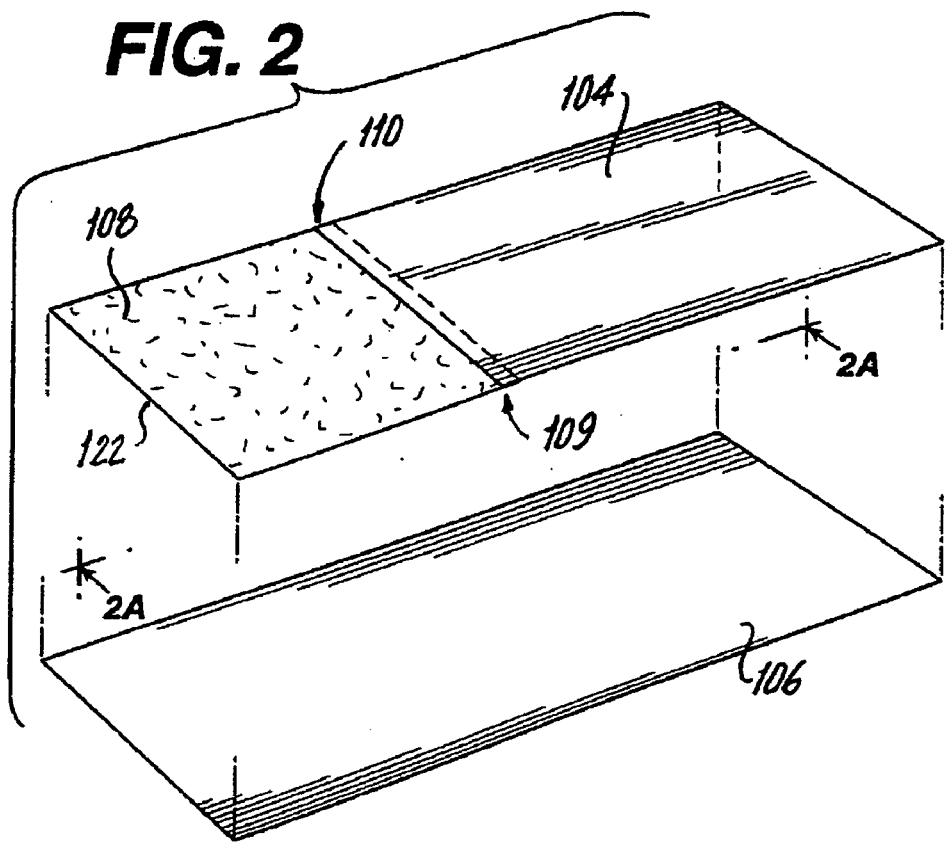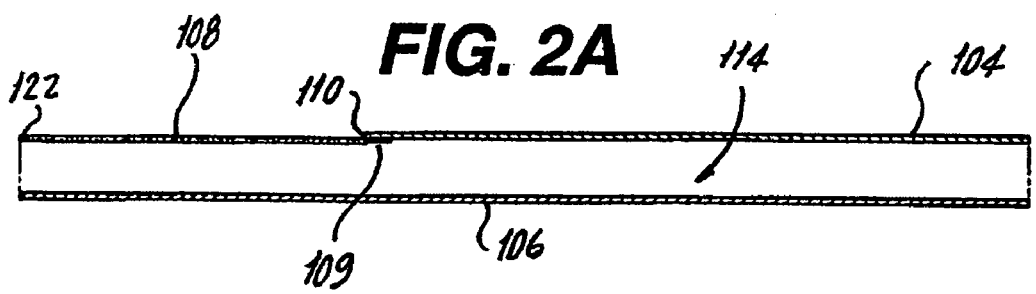

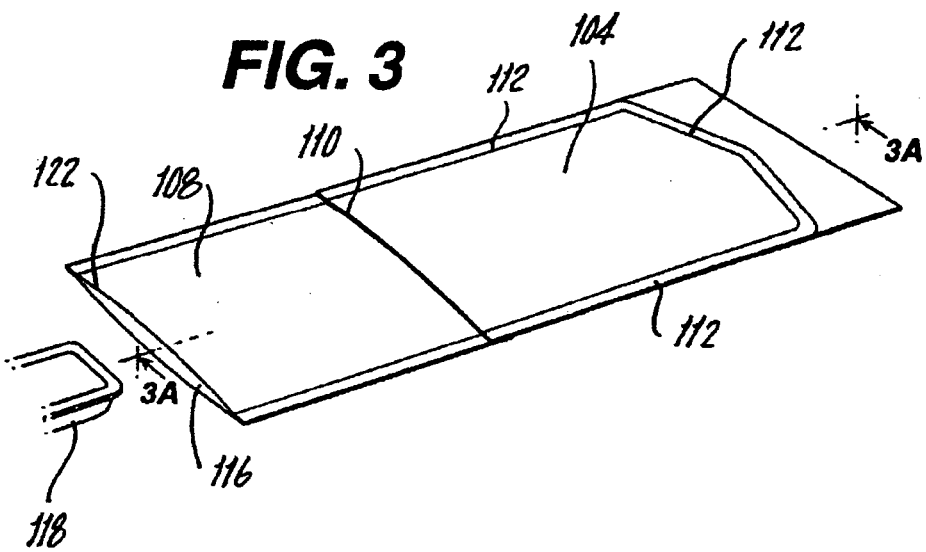
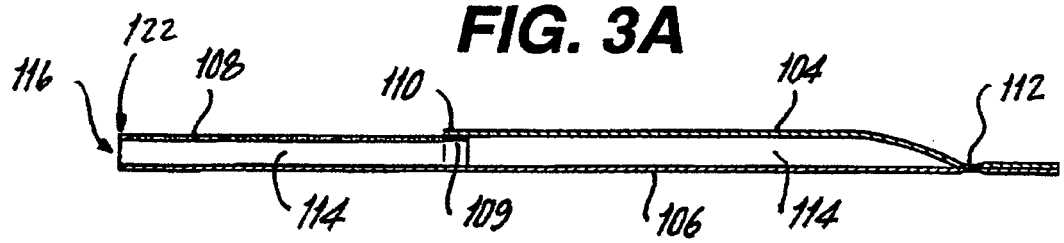

METHOD AND APPARATUS FOR PACKAGING A DRUG-DEVICE COMBINATION PRODUCT

This application is a divisional application of U.S. application Ser. No. 10/676,333 filed on Sep. 30, 2003, now pending, the disclosure of which is hereby incorporated herein by reference.

BACKGROUND OF THE INVENTION

1. Field of the Invention

This invention relates to a package for a drug-device combination product having an outer package including a first gas impermeable sheet, a second gas impermeable sheet and a gas permeable header.

2. Discussion of the Related Art

Packaging a product in an inner package and then packing the inner package in an outer package is common in the packaging arts. Vacuum packaging, packaging with an inert gas and multiple methods of sterilizing medical products are known in the medical device packaging art. However, drug-device combination products offer a new and unique problem in the packaging and sterilizing of the product, while refraining from altering the chemical structure of the drug incorporated in the device.

Numerous inventions relate to the use of radiation to sterilize products for medical use, for example, U.S. Pat. No. 5,577,368 to Hamilton et al. ("Hamilton") and U.S. Pat. No. 6,174,934 to Sun et al. ("Sun"). Both Hamilton and Sun first remove the oxygen/atmosphere from the packaging prior to radiation sterilizing medical implants made of polymeric material. Hamilton's and Sun's goal is to reduce the wear resistance of the polymeric implant and, radiation typically alters the chemical structures of incorporated drugs.

Other inventions known in the art require numerous complex steps to sterilize and seal a medical device in one or more packages. U.S. Pat. No. 4,709,819 to Lattuada et al. discloses first sterilizing an outer package, placing an inner package in the outer package and then evacuating both the inner and outer packages. This process is used because Lattuada et al. are packaging biological samples and any sterilization of the inner package would kill the sample.

Further, U.S. Pat. No. 4,941,308 to Grabenkort et al. discloses sterilizing the interior of the package before placing the product in the inner package, sterilizing the product in the inner package, and then placing the inner package in the outer package. Additionally, Grabenkort et al. uses ethylene oxide gas (EtO) for the sterilization.

Both Lattunda et al. and Grabenkort et al. require a separate sterilizing step prior to inserting and sealing the inner package in the outer package. This adds steps and cost to the handling of the already sterilized product/inner package prior to inserting it into the outer package.

Thus, there is a need in the art for a packaging product and method to sterilize a drug-incorporated device in the minimum number of steps while refraining from altering the chemical structure of the drug incorporated in the device.

SUMMARY OF THE INVENTION

A package for a drug-device combination product includes an outer package, including a first gas impermeable sheet and a second gas impermeable sheet hermetically sealed on three sides. The impermeable sheet material should be flexible and can be selected from among many types of high barrier, flexible packaging materials that are commonly used to enclose medical devices. Preferably the impermeable sheet material is a multilayered, heat seal peelable packaging material that includes one or more foil layers, various polymer layers and a heat seal coating. Examples of suitable materials are those that include the following layers: polyester film-low density polyethylene-foil-ionomer-heat seal coating. Packaging materials having the following layers can also be used: polyester-low density polyethylene-foil-EAA-linear low density polyethylene-heat seal coating; and polyester-Surlyn-nylon-Surlyn-foil-EAA-linear low density polyethylene-heat seal coating. Additionally, polyvinylidene chloride (PVDC) and ethylene vinyl alcohol copolymer, (EVOH), are genrally key components of a high-barrier film. Nylons, acrylonitrile methacrylate copolymer (AN-MA), and other specialty polymers such as certain copolyesters may potentially be used.

A gas permeable header is attached to an unsealed side of the first gas impermeable sheet and sealed to the second gas impermeable sheet on two sides. The first and second gas impermeable sheets and the gas permeable header form an interior and an opening that communicates with the interior to form three sealed sides of the outer package.

A gas permeable inner package is sized to fit the device and disposed within the outer package and preferable disposed only between the first and second gas impermeable sheets. The gas permeable material for both the header and/or the inner package can be Tyvek® or any other durable gas permeable material such as polyethylene, polystyrene or polypropylene. The gas permeable inner package can be a blister tray, a pouch, or any other gas permeable container designed to hold a product to be sterilized. The product can be incorporated with drugs that are antimicrobial agents, antiangiogenesis, antiproliferatives, and anti-inflammatorys. Incorporating the drug into the product can include, but is not limited to, impregnating, coating and sandwiching the drug between layers of the device.

In an embodiment of the product, the antimicrobial agent can be selected from the group comprising antibiotics, antiseptics, and disinfectants. Further, the antibiotics can be selected from a group comprising tetracyclines (i.e. minoclcine), penicillins, (i.e. nafcillin), macrolides (i.e. erythromycin), rifampin, gentamicin, vancomycinclindamycin, azithromycin, enoxacin, and combinations thereof. A preferred product is incorporated with Rifampicin or Clindamycin.

Antiangiogenesis drugs (also called angiogenesis inhibitors) deprive the cancer cells of their blood supply. Antiangiogenesis can be selected from the group including angiostatin, thalidomide (Thalomid™), CC-5013 (Revimid™), bevacizumab (Avastin™), squalamine, endostatin, angiostatin, and angiozyme. Other antiangiogenesis drugs can include drugs derived from chemotherapy drugs, for example, paclitaxel (Taxol™), doxorubicin (Adriamycin™), epirubicin, mitoxantrone, and cyclophosphamide.

Antiproliferative drugs can prevent restenosis (a re-narrowing or blockage of an artery at the same site where treatment, such as an angioplasty or stent procedure, has already taken place) of the implanted device. Examples of antiproliferatives are Sirolimus™ and Paclitaxel™. Examples of anti-inflammatories, including non-steroidal anti-inflammatory drugs (NSAID's), are ibuprofen, ketoprofen, motrin, and naproxen.

Once the product is sealed within the inner package, the inner package is placed within the outer package and a top end of the header is sealed to the second sheet. This forms a sealed outer package that has gas permeable and impermeable sections. Up to this point, only minimal care is required, neither the product, inner package, nor outer package has been sterilized and special handling or handling in a clean environment is not required. However, a preferred embodiment includes handling in a clean room environment to minimize the introduction of contaminants.

The sterilizing compound is then introduced into the interior of the outer package through the header. Since the inner package is also permeable, the sterilizing compound can permeate through the inner package and sterilize the product. As above, the sterilizing compound can be steam, ethylene oxide gas (EtO), gas plasma/radio frequency-peroxide (e.g. Sterrad™), chemical vapor (e.g alcohol, formaldehyde, etc), and cold sterilization using liquid chemical sterilants/disinfectants that require immersion (e.g. glutaraldehyde and chlorine dioxide). The invention allows for any sterilization process that utilizes a sterilizing agent that can only pass through a permeable layer.

Once the product is sterilized, the atmosphere can be evacuated from the interior to 'vacuum seal' the product, as well as retard further oxidation. The outer package is then sealed by sealing the first gas impermeable sheet to the second gas impermeable sheet at a seal point below the point where the header attaches to the first sheet. The outer package is now a gas impermeable package. The header can either be removed or folded over to complete the packaging.

A key feature of the sterilizing step includes using any sterilizing process that maintains a chemical structure of the drug as well as prevents oxidation of the drug, and still sterilizes the product for medical use.

BRIEF DESCRIPTION OF THE DRAWING FIGURES

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein:

FIG. 1 is an exploded perspective view of the outer package of the present invention;

FIG. 2 is a perspective view of the outer package of the present invention;

FIG. 2A is a cross-sectional view along line 2A—2A of FIG. 2;

FIG. 3 is a perspective view of the of the assembled outer package prior to the insertion of the inner package;

FIG. 3A is a cross-sectional view along line 3A—3A of FIG. 3;

Figure 4:
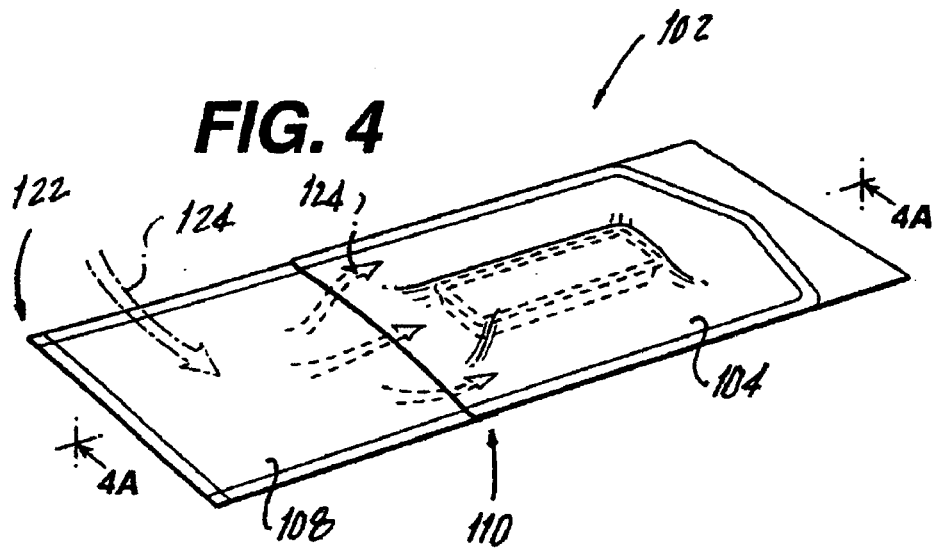
Figure 4A:
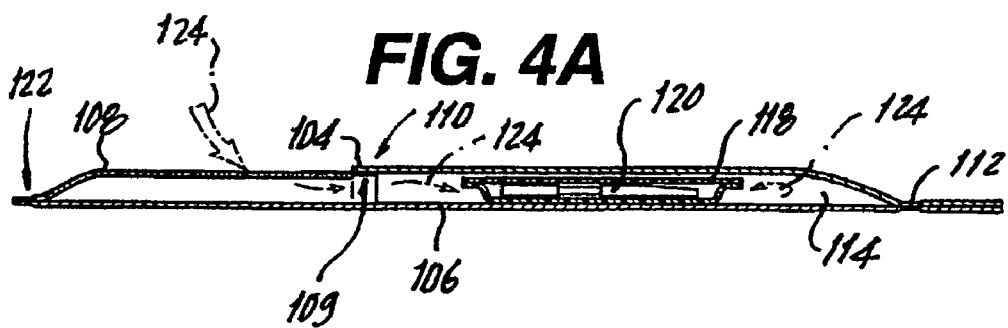
Figure 5:
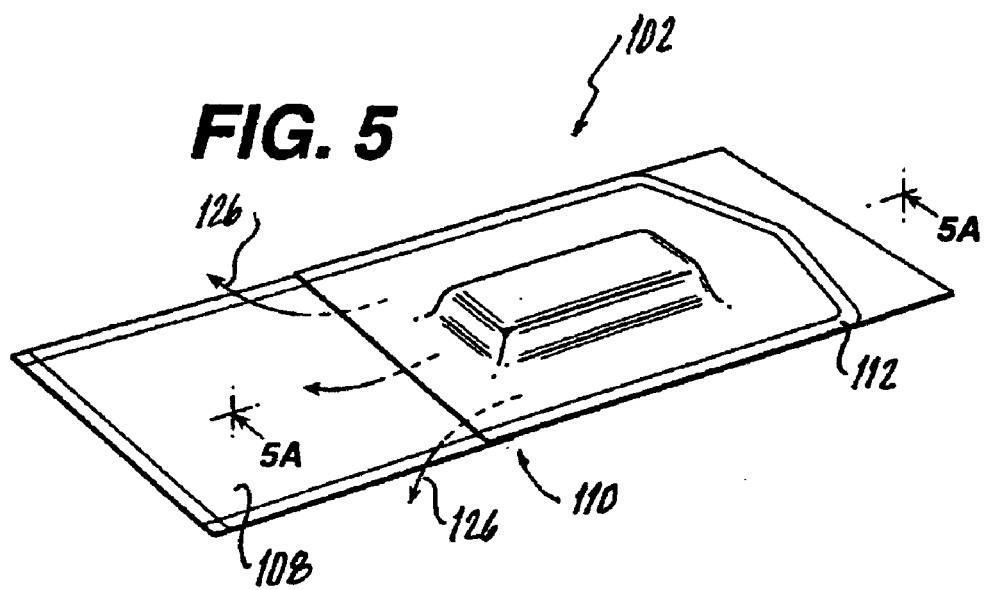
Figure 5A:
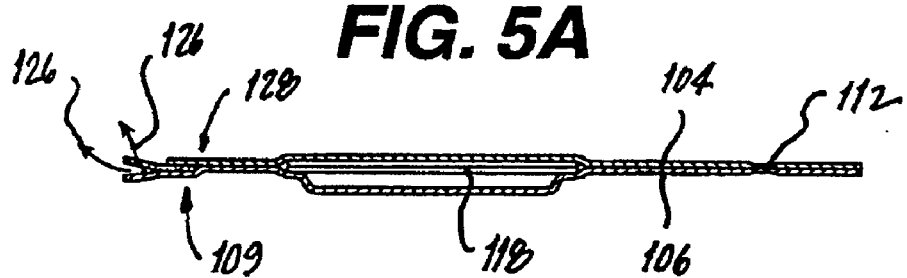
Figure 6:
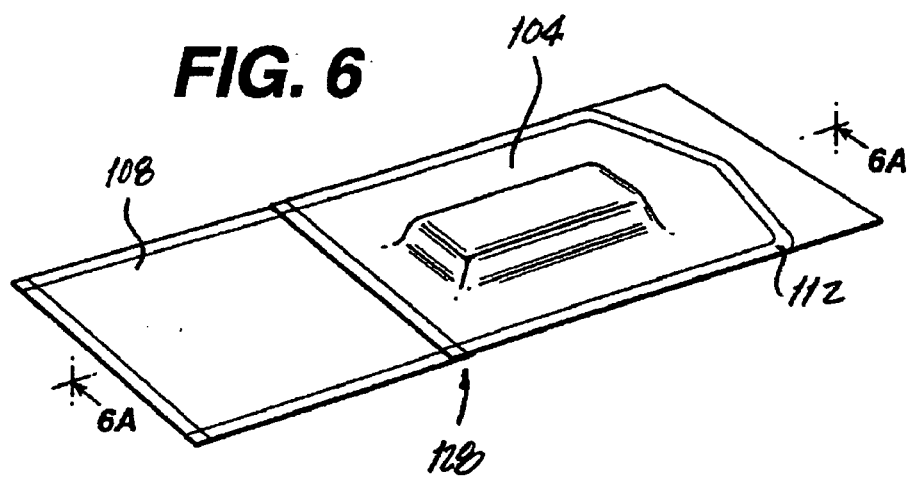
Figure 6A:
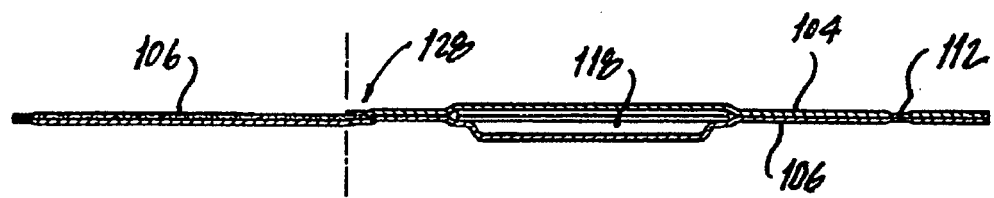
Figure 7:
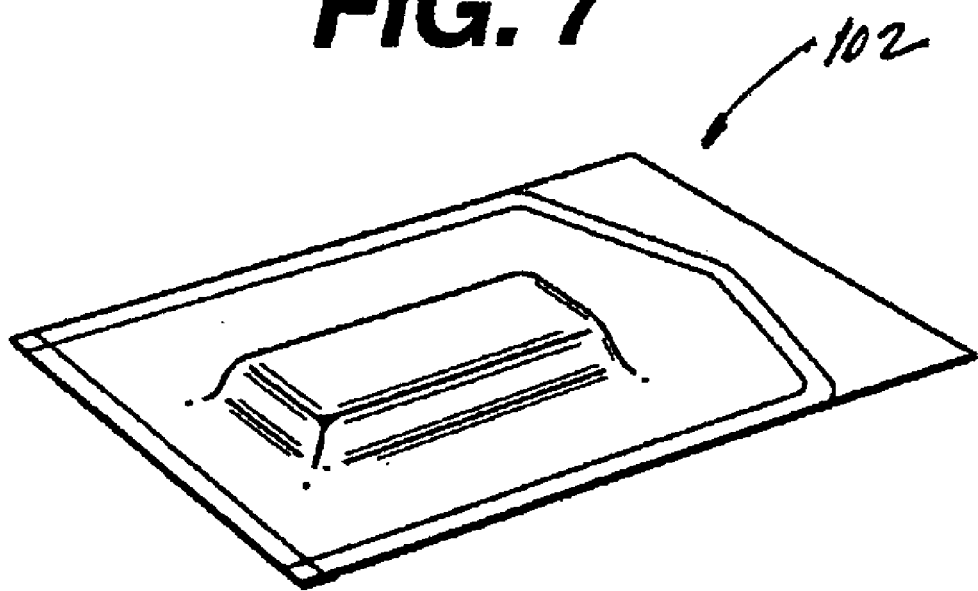

FIG. 4 a perspective view of the of the inner package and outer package during sterilization;

FIG. 4A is a cross-sectional view along line 4A—4A of FIG. 4;

FIG. 5 is a perspective view of the inner package and outer package during evacuation;

FIG. 5A is a cross-sectional view along line 5A—5A of FIG. 5;

FIG. 6 is a perspective view of the inner package and outer package after evacuation;

FIG. 6A is a cross-sectional view along line 6A—6A of FIG. 6;

FIG. 7 is a perspective view of the final packaging; and

Figure 8:
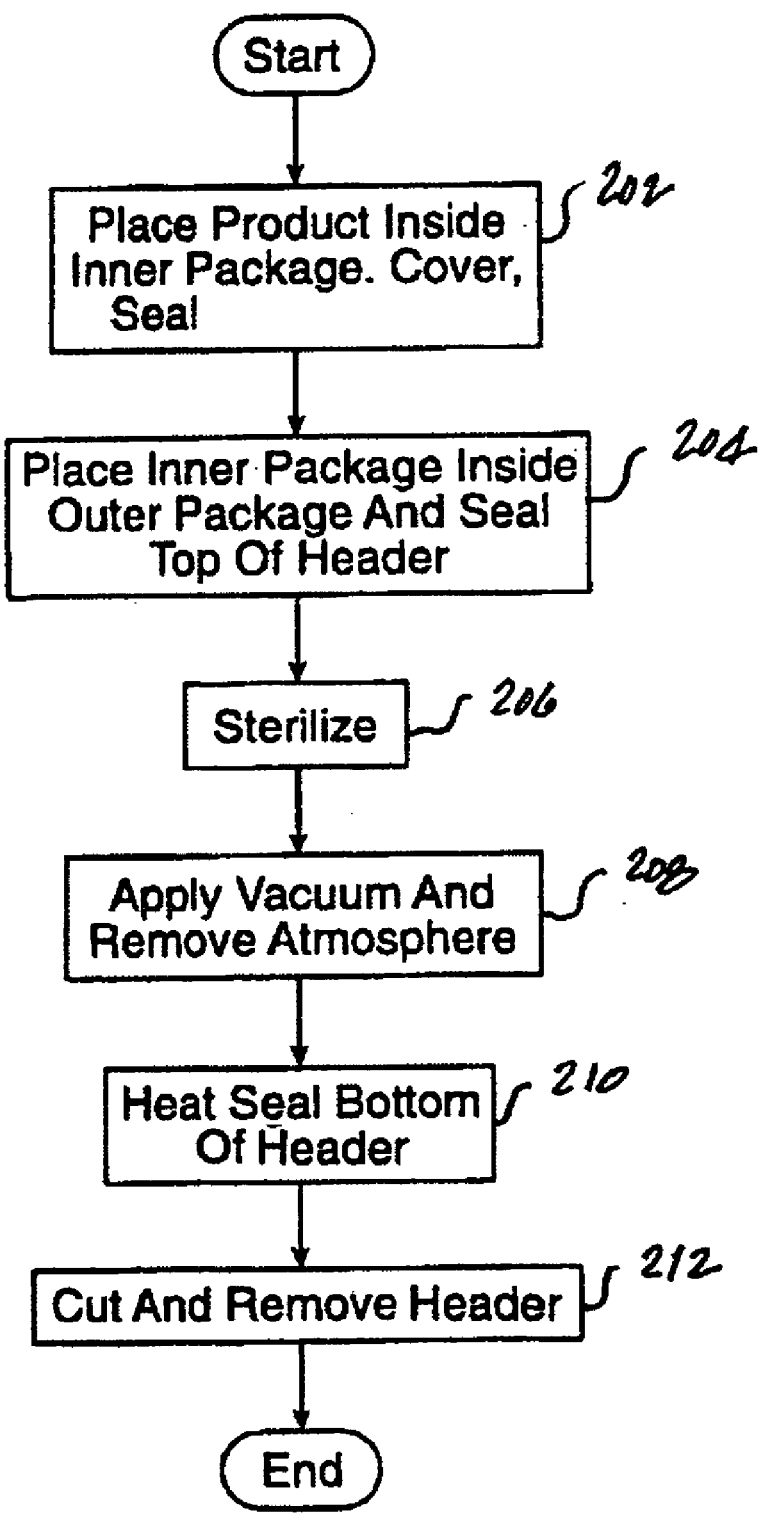

FIG. 8 is a flow chart outlining the method of the present invention.

DETAILED DESCRIPTION OF THE PREFERRED EMBODIMENT

Referring now to FIGS. 1 through 3A, a package 100 for a drug-device combination product is illustrated. Package 100 includes an outer package 102 including a first gas impermeable sheet 104 and a second gas impermeable sheet 106 hermetically sealed on three sides 112 (FIG. 3). A gas permeable header 108 is attached at an attachment point 109 located on an unsealed side 110 of first gas impermeable sheet 104 and sealed to second gas impermeable sheet 106 on two sides. First and second gas impermeable sheets 104, 106 and gas permeable header 108 form an interior 114 with an opening 116 communicating with interior 114. The impermeable sheet material should be flexible and can be selected from among many types of high barrier, flexible packaging materials that are commonly used to enclose medical devices. Preferably the impermeable sheet material is a multilayered, heat seal peelable packaging material that includes one or more foil layers, various polymer layers and a heat seal coating. Examples of suitable materials are those that include the following layers: polyester film-low density polyethylene-foil-ionomer-heat seal coating. Packaging materials having the following layers can also be used: polyester-low density polyethylene-foil-EAA-linear low density polyethylene-heat seal coating; and polyester-Surlyn-nylon-Surlyn-foil-EAA-linear low density polyethylene-heat seal coating. Additionally, polyvinylidene chloride (PVDC) and ethylene vinyl alcohol copolymer, (EVOH), are genrally key components of a high-barrier film. Nylons, acrylonitrile methacrylate copolymer (AN-MA), and other specialty polymers such as certain copolyesters may potentially be used.

Referring to FIGS. 3 through 4A, a gas permeable inner package 118 is disposed within outer package 102. Additionally, gas permeable inner package 118 is preferably disposed only between first and second gas impermeable sheets 104, 106. The gas permeable material for both the header and/or the inner package can be Tyvek® or any other durable gas permeable material such as polyethylene, polystyrene or polypropylene. Gas permeable inner package 118 can be a blister tray, a pouch, or any other gas permeable container designed to hold a product 120 to be sterilized.

FIG. 4A illustrates product 120 which, in an embodiment, can be incorporated with a drug (not illustrated) and gas permeable inner package 118 is sized to contain product 120 and be placed only between gas impermeable section of first sheet and second sheet 104, 106. The drugs that the product can be incorporated with are antimicrobial agents, antiangiogenesis, antiproliferatives, and anti-inflammatorys. Incorporating the drug into the product can include, but is not limited to, impregnating, coating and sandwiching the drug between layers of product 120.

In an embodiment of product 120, the antimicrobial agent can be selected from the group comprising antibiotics, antiseptics, and disinfectants. Further, the antibiotics can be selected from a group comprising tetracyclines (i.e. Minoclcine™), penicillins, (i.e. Nafcilin™), macrolides (i.e. Erythromycin™), rifampin, gentamicin, vancomycinclindamycin, azithromycin, enoxacin, and combinations thereof. A preferred product 120 is incorporated with Rifampicin™ or Clindamycin™.

Antiangiogenesis drugs (also called angiogenesis inhibitors) deprive the cancer cells of their blood supply. Antiangiogenesis can be selected from the group including angiostatin, thalidomide (Thalomid™), CC-5013 (Revimid™), bevacizumab (Avastin™), squalamine, endostatin, angiostatin, and angiozyme. Other antiangiogenesis drugs can include drugs derived from chemotherapy drugs, for example, paclitaxel (Taxol™), doxorubicin (Adriamycin™), epirubicin, mitoxantrone, and cyclophosphamide.

Antiproliferative drugs can prevent restenosis (a re-narrowing or blockage of an artery at the same site where treatment, such as an angioplasty or a stent procedure, has already taken place) of product 120. Examples of antiproliferatives are Sirolimus™ and Paclitaxel™. Examples of anti-inflammatories, including non-steroidal anti-inflammatory drugs (NSAID's), are ibuprofen, ketoprofen, motrin, and naproxen.

FIGS. 3 through 4A further illustrate that once product 120 is sealed within inner package 118, inner package 118 is placed within outer package 102. A top end 122 of header 108 is sealed to second sheet 106. A sterilizing compound 124 is then introduced into interior 114 through header 108. Sterilizing compound 124 then permeates through inner package 118 and sterilizes product 120. Sterilizing compound 124 can be steam, ethylene oxide gas (EtO), gas plasma/radio frequency-peroxide (e.g. Sterrad™), chemical vapor (e.g alcohol, formaldehyde, etc), and cold sterilization using liquid chemical sterilants/disinfectants that require immersion (e.g. glutaraldehyde and chlorine dioxide). The invention allows for any sterilization process that utilizes a sterilizing agent that can only pass through a permeable layer and that process is compatible with the incorporated drug. For example, Rifampicin is not compatible with EtO sterilization, but is compatible with steam sterilization.

Referring to FIGS. 5 and 5A, optionally, atmosphere 126 can be evacuated from interior 114 to 'vacuum seal' product 120. Outer package 102 is then sealed by sealing first gas impermeable sheet 104 to second gas impermeable sheet 106 at a seal point 128 below attachment point 109 of header 108 to first sheet 104. Outer package 102 is now a gas impermeable package. Optionally, header 108 can either be removed or folded over to complete the packaging (FIG. 7).

FIG. 8 illustrates a method of packaging a drug-device combination product 120 such as, for example, but not limited to a drug incorporated catheter (e.g. Bactiseal™) and a drug-eluting stent (e.g. Cypher™). The steps include placing product 120 inside gas permeable inner package 118 (step 202), sealing inner package 118, and placing inner package 118 inside outer package 102 (step 204). Outer package 102 is formed as described above. Further steps include sealing the top end 122 of header 108 to second sheet 106 to seal inner package 118 in outer package 102 (step 204). Once inner package 118 is sealed, product 120 is sterilized with sterilizing compound 126 (step 206) and the first sheet 104 is sealed to second sheet 106 to seal inner package 118 in a gas impermeable outer package (step 210). An embodiment includes, after the sterilizing step (206), removing atmosphere 126 from inside outer package 102 (step 208). Once the gas impermeable outer package is sealed, another step includes removing the gas permeable header 108 (step 212), or as an alternative header 108 can be folded under outer package 102.

An embodiment includes, replacing atmosphere 126 with an inert gas (not illustrated) prior to removing the atmosphere 128 (step 208). Another embodiment includes, after removing the atmosphere (step 208), filling the outer package 102 with an inert gas (not illustrated).

A key feature of the sterilizing step includes using steam, EtO, gas plasma/radio frequency-peroxide, chemical vapor, cold sterilization or any sterilizing process that maintains the chemical structure of the incorporated drug, prevents oxidation of the incorporated drug and also maintains the desired mechanical properties (rigidity, elasticity, etc.) of the device, while still sterilizing the product for medical use.

While there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

We claim:

1. A package for a drug-device combination product, comprising:
    an outer package comprising:
        a first gas impermeable sheet;
        a second gas impermeable sheet hermetically sealed on three sides with the first gas impermeable sheet;
        a gas permeable header disposed at an unsealed side of the first gas impermeable sheet and sealed to the second gas impermeable sheet on two sides; and
    wherein the first and the second gas impermeable sheets and the gas permeable header form an interior and an opening communicating with the interior; and
    a gas permeable inner package designed to hold said drug-device combination product and be disposed within the outer package.

2. The package of claim 1, wherein the gas permeable inner package is disposed only between the first and the second gas impermeable sheets.

3. The package of claim 1, wherein the gas permeable inner package is a blister tray.

4. The package of claim 1, wherein the gas permeable inner package is a pouch.

5. A package for a product, comprising:
    a product incorporated with a drug;
    a gas permeable inner package sized to contain the product; and
    an outer package comprising:
        a first sheet comprising:
        a gas impermeable section; and
        a gas permeable header disposed to a first side of the gas impermeable section;
        a second sheet being gas impermeable and hermetically sealed on three sides to the first sheet; and
        the first and the second sheets forming an interior and an opening communicating with the interior, wherein the inner package is disposed within the outer package.

6. The package of claim 5, wherein the gas permeable inner package is disposed only between the gas impermeable section of the first sheet and the second sheet.

7. The package of claim 5, wherein the gas permeable inner package is a blister tray.

8. The package of claim 5, wherein the gas permeable inner package is a pouch.

9. The package of claim 5, wherein the drug is selected from the group comprising antimicrobial agents, antiangiogenesis, antiproliferatives, and anti-inflammatorys.

10. The package of claim 9, wherein the antimicrobial agents are selected from the group comprising antibiotics, antiseptics, and disinfectants.

11. The package of claim 10, wherein the antibiotics are selected from the group comprising tetracyclines, penicillins, macrolides, rifampin, gentamicin, vancomycinclindamycin, azithromycin, enoxacin, and combinations thereof.

12. The package of claim 9, wherein the antimicrobial agent is at least one of Rifampicin and Clindamycin.

13. The package of claim 9, wherein the antiangiogenesis are selected from the group comprising angiostatin, thalidomide, CC-5013, bevacizumab, squalamine, endostatin, angiostatin, angiozyme, paclitaxel, doxorubicin, epirubicin, mitoxantrone, and cyclophosphamide.

14. The package of claim 9, wherein the antiproliferatives is at least one of Sirolimus and Paclitaxel.

15. The package of claim 9, wherein the anti-inflanimatorys are selected from the group comprising ibuprofen, ketoprofen, motrin, or naproxen.

* * * * *